United States Patent [19]

Takagaki et al.

[11] Patent Number: 4,525,303
[45] Date of Patent: Jun. 25, 1985

[54] PROCESS FOR PREPARATION OF STEROIDS

[75] Inventors: Hidetsugu Takagaki, Ichihara; Shigenori Nakanishi, Chiba; Yasuyuki Tanaka, Tokyo; Michihiro Watanabe, Ichihara; Yoriko Yonehara, Ohmiya, all of Japan

[73] Assignee: Dainippon Ink and Chemicals Inc., Tokyo, Japan

[21] Appl. No.: 505,292

[22] Filed: Jun. 17, 1983

[30] Foreign Application Priority Data

Jun. 21, 1982 [JP] Japan .................................. 57-105367
Dec. 27, 1982 [JP] Japan .................................. 57-227076
Dec. 27, 1982 [JP] Japan .................................. 57-227077

[51] Int. Cl.³ .............................................. C07J 21/00
[52] U.S. Cl. .................. 260/239.55 R; 260/239.55 C; 260/397.45
[58] Field of Search .................... 260/397.45, 239.55 R

[56] References Cited

U.S. PATENT DOCUMENTS

| | | | |
|---|---|---|---|
| 2,779,775 | 1/1957 | Sarett | 260/397.45 |
| 4,189,440 | 2/1980 | Palladino | 260/397.45 |
| 4,221,786 | 9/1980 | Kalvoda | 260/397.45 |
| 4,272,446 | 6/1981 | Riva et al. | 260/397.45 |
| 4,340,538 | 7/1982 | Shephard | 260/397.45 |

Primary Examiner—Elbert L. Roberts
Attorney, Agent, or Firm—Sherman & Shalloway

[57] ABSTRACT

A novel process for preparing a steroid of the following formula (to be referred to as compound ⑬ ) is provided.

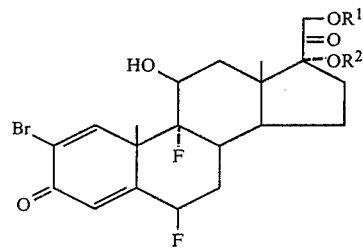

This compound is known to have marked anti-inflammatory and anti-rheumatoid arthritic activity with very much reduced side effects on humans, such as weight loss, sodium retention, potassium loss and adrenal and pituitary inhibition which are observed in many steroids. The process is characterized in that starting from hydrocortisone, it can produce the desired compound ⑬ at low cost and that it goes through the following two novel compounds (I) and (II) as intermediates.

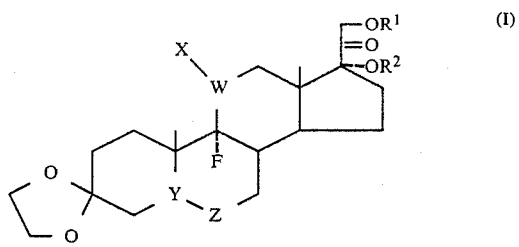

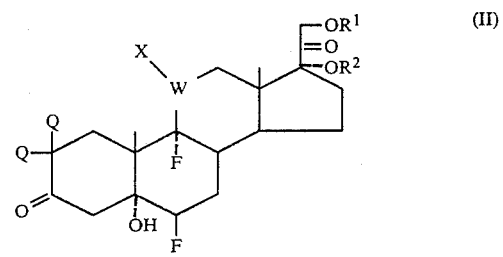

In the above formulae, $>$W—X represents $>$C$=$O or $>$CH—OH, $>$Y—Z— represents $>$C$=$CH— or

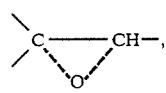

Q represents a hydrogen or bromine atom, and $OR^1$ and $OR^2$ are identical or different and each represents an acyloxy group or a sulfuric or phosphoric acid ester residue.

14 Claims, No Drawings

PROCESS FOR PREPARATION OF STEROIDS

This invention relates to a new process for preparing 2-bromo-6β,9α-difluoro-11β,17α,21-trihydroxy-1,4-pregnadien-3,20-dione-17,21-diesters.

The 2-bromo-6β,9α-difluoro-11β,17α,21-trihydroxy-1,4-pregnadien-3,20-dione-17,21-diesters [to be referred to as compounds (13) hereinafter] produced by this invention are known to have valuable pharmacological activities, especially anti-inflammatory and anti-rheumatoid arthritic activity with very much reduced side effects such as weight loss, sodium retention, potassium loss and adrenal and pituitary inhibition which are observed in various known biologically active steroids (see U.S. Pat. No. 4,226,862). Their anti-rheumatoid activity by intra-articular injection has also been reported.

Some methods for preparing the compounds (13) have been known (see, for example, U.S. Pat. Nos. 4,226,862 and 4,189,440). According to these methods, the 11-epimer of hydrocortisone-21-ester is used as a starting material, and through a series of reactions including ketalization with ethylene glycol, epoxidation with a peracid and ring-opening of the epoxy, 6β-fluoro-5α,11α,17α,21-tetrahydroxypregna-3,20-dione-21-ester is obtained as an intermediate. The intermediate is then subjected to various reactions including bromination of the 2-position, formation of a double bond at the 1,2-position and 4,5-position, mesylation of the 11-hydroxyl group, acylation of 17-hydroxyl group, formation of a double bond at the 9,11-position, bromohydrin formation at the 9,11-position, epoxidation with a base, and ring-opening of the epoxy product with hydrogen fluoride, thereby to form the compound (13).

The above method of synthesizing the compound (13) is disadvantageous in that the starting 11-epihydrocortisone-21-ester is expensive and difficult to obtain. It is desirable therefore to synthesize compound (13) by using a material which is less costly and is easily available.

We have now found as a result of extensive investigations that compound (13) can be produced in good yields by starting from hydrocortisone-21-acetate which is less costly and more easily available than 11-epihydrocortisone-21-acetate.

The process for the preparation of compound (13) in accordance with this invention is shown by the following scheme 1.

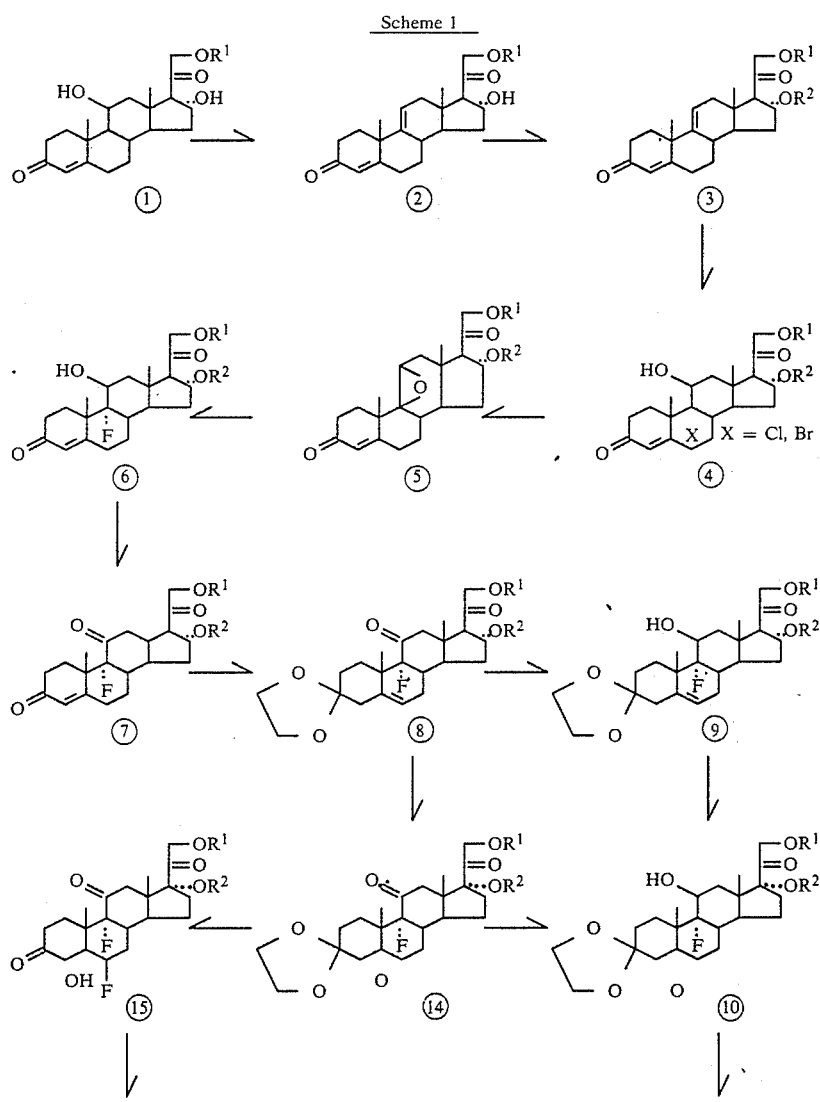

Scheme 1

Scheme 1

-continued

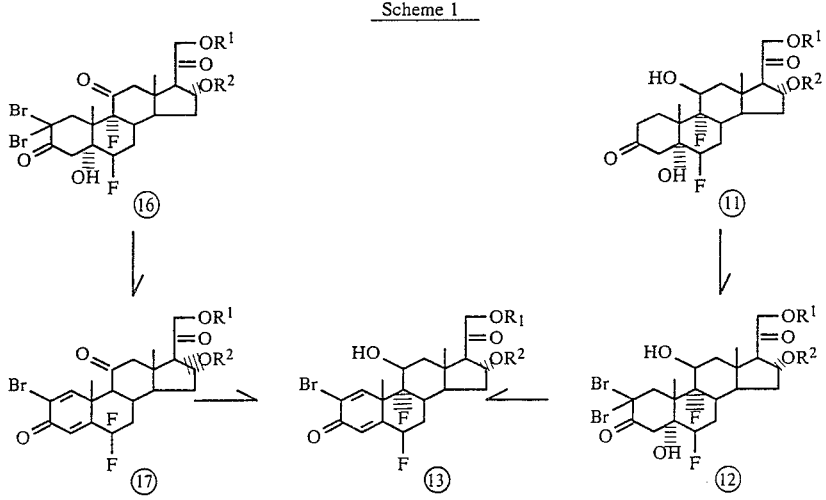

In the above scheme, OR¹ and OR² are identical or different, and each represents an acyloxy group or a residue of a sulfuric or phosphoric acid ester.

Among the compounds shown in the above scheme, compounds ⑧, ⑨, ⑩ and ⑭ are novel compounds which can be represented by the following general formula (I). Compounds ⑪, ⑫, ⑮ and ⑯ are also novel compounds represented similarly by general formula (II) below.

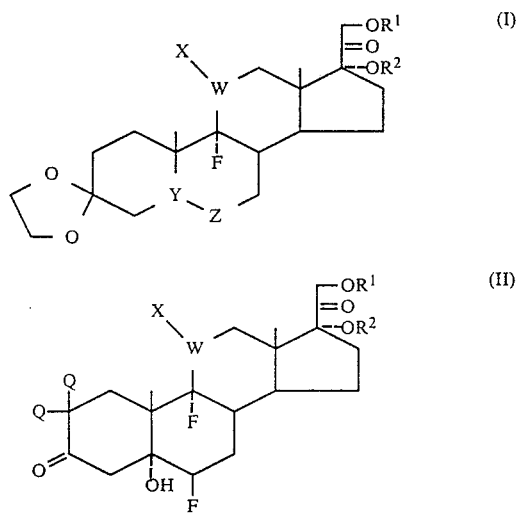

In the formulae, >W—X represents >C=O or >CH—OH, >Y—Z— represents >C=CH— or

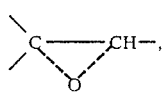

Q represents a hydrogen or bromine atom, and OR¹ and OR² are as defined above.

For the sake of convenience, the process of this invention is described below by taking up as an example the case of both R¹ and R² being acetyl groups. Compound ③ in which both R¹ and R² are acetyl groups is referred to as compound ③'. The other compounds will be referred to similarly.

Compound ③' as one starting material in this invention is a known compound which can be easily obtained in a high yield by first converting hydrocortisone-21-acetate (compound ①') into compound ②' by the action of pyridine and methanesulfonyl chloride in N,N-dimethylformamide, and then reacting compound ②' with an acetylating agent such as acetic anhydride or isopropenyl acetate in the presence of an acid catalyst such as perchloric acid or p-toluenesulfonic acid. In the prior art, the 11-hydroxyl group is converted to a Δ9(11) form by performing reactions in two stages through a 11-mesyloxy form. By using compound ①' as a starting material, this can be accomplished in one stage, and the reaction process can be shortened.

9α-Chloro or 9α-bromo-11β,17α,21-trihydroxy-4-pregnen-3,20-dione-17,21-diacetate (compound ④') can be obtained by reacting 17α,21-dihydroxy-4,9(11)-pregnadien-3,20-dione-17,21-diacetate (compound ③') with hypochlorous acid or hypobromous acid. The reaction is carried out by using a chlorinating or brominating agent in an acidic aqueous solution. N-chlorosuccinimide, N-bromosuccinimide, N-bromoacetamide, N-chloroacetamide, etc. may be used as the chlorinating or brominating agent. Examples of the acid are sulfuric acid and perchloric acid. As an auxiliary solvent for the reaction, an organic solvent may be used. The organic solvent may be any which does not react with the starting material nor with the product. Preferably, dioxane, tetrahydrofuran, acetone, etc. which are well compatible with water may be used. The reaction temperature is usually 0° to 50° C. although it varies depending upon the solvent, acid, and chlorinating or brominating agent used.

17α,21-Dihydroxy-9β,11β-epoxy-4-pregnen-3,20-dione-17,21-diacetate (compound ⑤') can be obtained by reacting compound ④' with a basic substance. Preferred basic substances include non-nucleophilic tertiary amines such as triethylamine and pyridine, alkali metal carbonates and alkali metal bicarbonates. The reaction is carried out by adding the basic substance to the isolated compound ④' or the reaction mixture containing compound ④', and heating the mixture at a temperature of 0° to 80° C., preferably 40° to 80° C.

9α-Fluoro-11β,17α,21-trihydroxy-4-pregnen-3,20-dione-17,21-diacetate (compound ⑥') can be obtained by reacting compound ⑤' with hydrogen fluoride.

Preferably, hydrogen fluoride is introduced in the form of an aqueous solution into the reaction system. Preferably, the reaction is carried out at a low temperature, of, for example, 0° to −80° C. The reaction is carried out by adding compound ⑤' either as such or as a solution in an organic solvent to an aqueous solution of hydrogen fluoride. The organic solvent used at this time may be any which does not react with compounds ⑤' and ⑥' or hydrogen fluoride. Preferably, solvents having a good dissolving power for compound ⑤', such as tetrahydrofuran and chloroform, are used.

17α,21-Dihydroxy-9α-fluoro-4-pregnen-3,11,20-trione-17,21-diacetate (compound ⑦') can be obtained by oxidizing compound ⑥'. Suitable oxidizing agents are chromium compounds such as chromic anhydride and sodium bichromate, and dimethyl sulfoxide (DMSO). The reaction is carried out in a solvent. The kind of solvent varies with the oxidizing agent used. Pyridine is preferred as the solvent when chromic anhydride is used as the oxidizing agent, and a mixture of acetic acid and water, when sodium bichromate is used as the oxidizing agent. When the oxidation is carried out using DMSO, DMSO may be used as the solvent. Or other organic solvents such as tetrahydrofuran, methylene chloride or chloroform may be used in combination. Oxidation with DMSO requires the presence of a dehydrating agent. Suitable dehydrating agens are acid anhydrides or acid halides. Examples of preferred acid anhydrides are acetic anhydride, trichloroacetic anhydride, trifluoroacetic anhydride, sulfuric anhydride and methanesulfonic anhydride. Examples of preferred acid halides are acetyl chloride, acetyl bromide, benzoyl chloride, oxalyl chloride, methanesulfonyl chloride and p-toluenesulfonyl chloride. The reaction temperature is between −20° C. and 40° C. in the case of oxidation with chromium compounds. In the case of oxidation with DMSO, the reaction temperature varies with the dehydrating agent used, and is between −80° C. and 100° C. The above process gives compound ⑦' in high yields.

17α,21-Dihydroxy-3,3-ethylenedioxy-9α-fluoro-5-pregnen-11,20-dione-17,21-diacetate (compound ⑧') can be obtained by reacting compound ⑦' with ethylene glycol or its derivative in the presence of an acid catalyst. Examples of the acid catalyst include sulfonic acids such as p-toluenesulfonic acid and trifluoromethanesulfonic acid, and sulfonic acid resins such as Amberlist 15 (a tradename for a product of Rohm & Haas Co.). Examples of useful ethylene glycol derivatives are ketal derivatives of carbonyl compounds such as acetone ethylene ketal and mesityl oxide ethylene ketal, and ketalization agents such as ethylene glycol ditrimethylsilyl ether. The reaction is carried out in an organic solvent. The organic solvent may be any which does not react with the starting material and the product. Examples of suitable organic solvents are benzene, tetrahydrofuran and chloroform. The reaction temperature differs depending upon the type of the acid catalyst or ketalization agent used, but is usually in the range of −20° C. to 100° C. Better results are obtained when a dehydrating agent such as molecular sieves and calcium sulfate is used as a reaction aid.

3,3-Ethylenedioxy-9α-fluoro-11β,17α,21-trihydroxy-5-pregnen-20-one-17,21-diacetate (compound ⑨') can be obtained by subjecting compound ⑧' to the action of a reducing agent. Sodium borohydride is suitable as the reducing agent because of its low cost and good stereo-selectivity. The reaction is carried out in a solvent, preferably an amide-type polar solvent such as N,N-dimethylformamide or N-methylpyrrolidone, or a mixture of water and an organic solvent, such as tetrahydrofuran-water or dioxane-water. The reaction can be carried out at a temperature between 0° and 50° C. Preferably, by carrying it out at a mild temperature between 0° and 30° C., side-reactions can be prevented.

5α,6α-Epoxy-3,3-ethylenedioxy-11β,17α,21-trihydroxypregna-20-one-17,21-diacetate (compound ⑩') can be obtained by subjecting compound ⑨' to the action of a peracid. Examples of the peracid include peracetic acid, pertrifluoroacetic acid, m-chloroperbenzoic acid, perbenzoic acid and permonophthalic acid. The reaction is carried out in an organic solvent which does not react with the starting material and the product. Usually, halogen-containing solvents such as methylene chloride and chloroform are used. Preferably, the reaction is carried out usually at a temperature between −20° C. and 50° C.

6β,9α-Difluoro-5α,11β,17α,21-tetrahydroxypregna-3,20-dione-17,21-diacetate (compound ⑪') can be obtained by treating compound ⑩' with an aqueous solution of hydrogen fluoride. The reaction is carried out by adding compound ⑩' as such or in the form of an organic solvent solution to the aqueous solution of hydrogen fluoride. The organic solvent used at this time is one which well dissolves the starting compound ⑩', such as tetrahydrofuran and chloroform. The reaction is carried out at a temperature in the range of 0° to −80° C., preferably −20° to −80° C.

2,2-Dibromo-6β,9α-difluoro-5α,11β,17α,21-tetrahydroxypregna-3,20-dione-17,21-diacetate (compound ⑫') can be obtained by brominating compound ⑪'. Bromine and N-bromosuccinimide are examples of a brominating agent used in this reaction. This brominating reaction is carried out in the co-presence of a basic compound such as sodium acetate and potassium acetate. Preferably, the reaction is carried out in acetic acid. The reaction can be carried out at a temperature between 0° and 120° C., preferably between 80° and 120° C.

2-Bromo-6β,9α-difluoro-11β,17α,21-trihydroxy-1,4-pregnadien-17,21-diacetate (compound ⑬') can be obtained by heating compound ⑫' to dehydrobrominate and dehydrate it. The reaction is carried out in an organic solvent. Suitable organic solvents include amide-type solvents such as N,N-dimethylformamide, N,N-dimethylacetamide and N-methylpyrrolidone. As a catalyst for dehydrobromination and dehydration, a metal halide, either alone or in combination with a metal carbonate, can be used. Suitable metal halides include lithium chloride and lithium bromide. Examples of the metal carbonate are alkali metal carbonates such as lithium carbonate and sodium carbonate, and alkaline earth metal carbonates such as calcium carbonate. The reaction is carried out at a high temperature of 80° to 160° C. To obtain better results, temperatures of 100° to 130° C. are preferred.

17α,21-Dihydroxy-5α,6α-epoxy-3,3-ethylenedioxy-9α-fluoropregna-11,20-dione-17,21-diacetate (compound ⑭') can be obtained by reacting compound ⑧' with a peracid as in the reaction of forming compound ⑩' from compound ⑨'. Treating compound ⑭' with a reducing agent as in the reaction of forming compound ⑨' from compound ⑧' gives compound ⑩'.

6β,9α-Difluoro-5α,17α,21-trihydroxypregna-3,11,20-trione-17,21-diacetate (compound ⑮') can be obtained by treating compound ⑭ ' with hydrogen fluoride as in the reaction of forming compound ⑪ ' from compound ⑩ '.

2,2-Dibromo-6β,9α-difluoro-5α,17α,21-trihydroxypregna-3,11,20-trione-17,21-acetate (compound ⑯ ') can be obtained by brominating compound ⑮ ' as in the reaction of forming compound ⑫ ' from compound ⑪ '.

2-Bromo-6β,9α-difluoro-17α,21-dihydroxy-1,4-pregnadien-3,11,20-trione-17,21-diacetate (compound ⑰ ') can be obtained by dehydrobrominating and dehydrating compound ⑯ ' as in the reaction of forming compound ⑬ ') from compound ⑫ '. Treatment of compound ⑰ ' with a reducing agent, as in the reaction of forming compound ⑨' from compound ⑧' or the reaction of forming compound ⑩ ' from compound ⑭ ', can give compound ⑬ '.

According to this invention, even when $OR^1$ and $OR^2$ in the above chemical formulae are ester residues other than the acetoxy group, compound ⑬ can be produced in substantially the same way as in the case of the acetoxy group by modification customarily practiced by those skilled in the art.

Examples of acids which constitute the other ester residues include inorganic acids such as sulfuric acid and phosphoric acid and organic acids such as sulfonic acids and carboxylic acids. The carboxylic acids include aliphatic, alicyclic, aromatic, araliphatic and heterocyclic carboxylic acids, thiocarboxylic acids and aminocarboxylic acids. Preferred carboxylic acids include formic acid, acetic acid, chloroacetic acid, trifluoroacetic acid, propionic acid, butyric acid, valeric acid, trimethylacetic acid, diethylacetic acid, caproic acid, crotonic acid, enanthic acid, caprylic acid, capric acid, palmitic acid, undecanoic acid, undecylenic acid, oxalic acid, succinic acid, glutaric acid, pimelic acid, tartaric acid, maleic acid, lactic acid, carbamic acid, glycine, alkoxycarboxylic acids, hexahydrobenzoic acid, cyclopentylpropionic acid, cyclohexylacetic acid, cyclohexylbutyric acid, benzoic acid, phthalic acid, phenylacetic acid, phenylpropionic acid, furane-2-carboxylic acid, nicotinic acid and isonicoticic acid. Especially preferred carboxylic acids are acetic acid, trimethylacetic acid, propionic acid β-phenylpropionic acid, α-phenylpropionic acid, valeric acid and dicarboxylic acids such as succinic acid. Methanesulfonic acid and toluenesulfonic acid are preferred as the sulfonic acid.

Compounds ⑬ in which $OR^1$ is an acyloxy group, especially the above-mentioned preferred carboxylic acid residues, are preferred because the 21-ester shows especially superior biological activity. Compounds ⑬ in which $OR^1$ is a polycarboxylic acid ester residue, an inorganic acid residue in the form of a water-soluble salt, or an inorganic acid residue convertible to a water-soluble salt form are especially preferred.

According to this invention, 2-bromo-6β,9α-difluoro-11β,17α,21-trihydroxy-1,4-pregnadien-3,20-dione-17,21-diesters (compounds ⑬) can be produced in high yields by the process different from the prior art.

The following Referential Examples and Examples further illustrate the process of this invention. It should be understood however that the present invention is not limited to these examples.

REFERENTIAL EXAMPLE 1

405 g (1 mole) of compound ①' was added to a mixture of 2 liters of N,N-dimethylformamide and 350 ml of pyridine, and with stirring at room temperature, 260 g of methanesulfonyl chloride was added. The reaction mixture was heated, maintained at 80° to 85° C. for 1 hour, and then cooled to room temperature. Methanol (7 liters) was added. The precipitated crystals were separated by filtration, washed with methanol and water, and dried under reduced pressure to give 340 g (yield 88%) of almost pure compound 2 ' (melting point 232°–236° C.).

REFERENTIAL EXAMPLE 2

350 g (0.906 mole) of compound ②' was added to 3.2 liters of 1,2-dichloroethane, and 16 g (0.084 mole) of p-toluenesulfonic acid monohydrate was added. While the solution was heated under reflux, 130.5 g (1.305 moles) of isopropenyl acetate was added dropwise over the course of about 1.5 hours. The mixture was further heated under reflux for 2 hours. The reaction mixture was cooled to room temperature, and an aqueous solution of sodium bicarbonate was added to separate the mixture. The organic layer was washed with water twice and concentrated under reduced pressure. The crude crystals obtained were recrystallized from benzene-hexane to give 349 g (yield 90%) of compound ③' as white crystals (melting point 224° to 229.5° C.).

REFERENTIAL EXAMPLE 3

180 g (0.42 mole) of compound ③' was added to a mixed solvent consisting of 1 liter of dioxane and 200 moles of water. With stirring at room temperature, 15 ml of 70% perchloric acid was added, and further 81 g (0.455 mole) of N-bromosuccinimide was added. The mixture was stirred at room temperature for 1 hour, and an aqueous solution of sodium bisulfite was added to decompose the excess of N-bromosuccinimide. Ethyl acetate was added to separate the mixture. The organic layer was washed with an aqueous solution of sodium bicarbonate and then with water, and concentrated to give crude crystals of compound ④'. The compound ④' was used in a subsequent reaction without purification.

Melting point: 105.5°–106° C. (decomp.).

IR, $cm^{-1}$ (KBr): 3370(m)(νOH); 1760(s), 1740(s), 1730(s), 1650(s)(νC=O); 1240(νC—O—C).

$H^1$NMR, δ(CDCl$_3$): 0.98(3H, s, 18CH$_3$), 1.74(3H, s, 19CH$_3$), 2.12(3H, s, CH$_3$CO—), 2.15(3H, s, CH$_3$CO—), 4.62(1H, d, J=17 Hz, —COCH$_2$OAC), 4.88(1H, d, J=17 Hz, —COCH$_2$OAC), 4.58–4.75(1H, m, C-11H), 5.73(1H, d, J=1.5 Hz, C-4H).

Elemental analysis for C$_{25}$H$_{33}$O$_7$Br: Calculated (%): C, 57.15; H, 6.33; Br, 15.21. Found (%): C, 57.30; H, 6.34; Br, 15.14.

REFERENTIAL EXAMPLE 4

The crude compound ④' obtained from 180 g (0.42 mole) of compound ③' in accordance with Referential Example 3 was added to 1 liter of acetone, and an aqueous solution of 75 g of potassium carbonate in 500 ml of water was added. The reaction solution was heated to 40° to 50° C., and stirred at this temperature for 4 hours. The reaction solution was cooled, and by adding chloroform, separated. The organic layer was washed with water until the aqueous layer became neutral. Then, the organic layer was concentrated under reduced pressure. Recrystallization of the resulting crude crystals from benzene-hexane gave 168 g (yield 90% based on compound ③') of compound ⑤' as white crystals.

Melting point: 189°–191° C.

IR, cm$^{-1}$(KBr): 1750(s), 1730(s), 1670(s)($\nu$C=O); 1620(m)($\nu$C=C); 1240(s)($\nu$C—O—C).

H$^1$NMR $\delta$(CDCl$_3$): 0.90(3H, s, 18CH$_3$), 1.41(3H, s, 19CH$_3$), 2.08(3H, s, CH$_3$CO—), 2.14(3H, s, CH$_3$CO—), 3.44(1H, s, C-11H), 4.70(1H, d, J=16 Hz, —COCH$_2$OAC), 4.89(1H, d, J=16 Hz, —COCH$_2$OAC), 5.76(1H, s, C-4H).

Elemental analysis for C$_{25}$H$_{32}$O$_7$: Calculated (%): C, 67.55; H, 7.26 Found (%): C, 67.47; H, 7.24

REFERENTIAL EXAMPLE 5

44.5 g (0.1 mole) of compound ⑤′ was dissolved in 50 ml of chloroform, and the solution was slowly added dropwise to 120 ml of a 65% aqueous solution of hydrofluoric acid cooled at −20° to −30° C. After the addition, the mixture was further stirred for 1 hour. The reaction mixture was slowly added to an aqueous solution of potassium carbonate to neutralize the hydrofluoric acid. Chloroform was added to separate the mixture. The organic layer was washed with water, and concentrated under reduced pressure to give crude crystals. Recrystallization from benzenehexane gave 41.8 g (yield 90%) of compound ⑥′ as white crystals.

Melting point: 180°-181° C.

IR, cm$^{-1}$(KBr): 3430(m)($\nu$OH); 1750(s), 1730(s), 1710(s), 1650(s)($\nu$C=O); 1620(m)($\nu$C=C); 1240(s)($\nu$C—O—C).

H$^1$NMR, $\delta$(CDCl$_3$): 0.95(3H, s, 18CH$_3$), 1.50(3H, s, 19CH$_3$), 2.05(3H, s, CH$_3$CO—), 2.13(3H, s, CH$_3$CO—), 4.20-4.50(1H, m, C-11H), 4.61(1H, d, J=15.3 Hz, —COCH$_2$OAC), 4.86(1H, d, J=15.3 Hz, —COCH$_2$OAC), 5.75(1H, s, C-4H).

Elemental analysis for C$_{25}$H$_{33}$O$_7$F: Calculated (%): C, 64.64; H, 7.16; F, 4.09. Found (%): C, 64.56; H, 7.15; F, 4.10.

REFERENTIAL EXAMPLE 6

46.5 g (0.1 mole) of compound ⑥′ was dissolved in 120 ml of acetic acid. To the solution was added dropwise slowly 120 ml of a 15% aqueous sulfuric acid solution of 14.9 g (0.05 mole) of sodium bichromate at less than 20° C. After the addition, the mixture was stirred for 2 hours. The reaction mixture was poured into 1.2 liters of water. The resulting precipitate was separated by filtration, washed with water, and dried to give 44.0 g (yield 95%) of compound ⑦′ as a white powder.

Melting point: 245.5°-255.5° C. (decomp.).

IR, cm$^{-1}$(KBr): 1740(s), 1730(s), 1680(s)($\nu$C=O); 1624(m)($\nu$C=C); 1240(s)($\nu$C—O—C).

H$^1$NMR $\delta$(CDCl$_3$): 0.83(3H, s, 18CH$_3$), 1.48(3H, s, 19CH$_3$), 2.14(6H, s, CH$_3$CO—), 4.66(1H, d, J=16.5 Hz, —COCH$_2$OAC), 4.78(1H, d, J=16.5 Hz, —COCH$_2$OAC), 5.82(1H, s, C-4H).

Elemental analysis for C$_{25}$H$_{31}$O$_7$F: Calculated (%): C, 64.92; H, 6.76; F, 4.11. Found (%): C, 64.79; H, 6.77; F, 4.10.

REFERENTIAL EXAMPLE 7

A solution of 15.6 g (0.2 mole) of dimethyl sulfoxide in 100 ml of methylene chloride was cooled to −65° to −70° C. and a solution of 31.5 g (0.15 mole) of trifluoroacetic anhydride in 100 ml of methylene chloride was added at the same temperature. After stirring for 10 minutes, a solution of 46.5 g (0.1 mole) of compound ⑥′ in 300 ml of methylene chloride was added at the same temperature. The mixture was stirred for 30 minutes. Triethylamine (40 g; 0.4 mole) was added dropwise and the mixture was heated to room temperature. Water was added to the reaction mixture to separate it. The organic layer was washed with water, and concentrated under reduced pressure. The resulting crude crystals were recrystallized from chloroform-hexane to give 43.9 g (yield 95%) of compound ⑦′ as white crystals. The product showed the same properties as the product obtained in Referential Example 6.

EXAMPLE 1

46.3 g (0.1 mole) of compound ⑦′ and 31.0 g (0.15 mole) of ethylene glycol ditrimethylsilyl ether were added to 300 ml of chloroform. 1.9 g (0.01 mole) of p-toluenesulfonic acid monohydrate was further added, and the mixture was stirred at room temperature for 1 day. The reaction mixture was added to a 5% aqueous solution of sodium bicarbonate for neutralization. It was then separated by standing. The organic layer was concentrated under reduced pressure. The crude crystals were recrystallized from chloroform-hexane to give 48.1 g (yield 95%) of compound ⑧′ as white crystals.

Melting point: 173.2°-175.0° C.

IR, cm$^{-1}$(KBr): 1758(s), 1740(s), 1732(s)($\nu$C=O); 1240($\nu$C—O—C).

H$^1$NMR, $\delta$(CDCl$_3$): 0.69(3H, s, 18CH$_3$), 1.27(3H, s, 19CH$_3$), 2.11(3H, s, CH$_3$CO—), 2.14(3H, s, CH$_3$CO—), 3.90(4H, s, —OCH$_2$CH$_3$O—), 4.64(1H, d, J=16.5 Hz, —COCH$_2$OAC), 4.78(1H, d, J=16.5 Hz, —COCH$_2$OAC), 5.25-5.45(1H, m, C-6H).

Elemental analysis for C$_{27}$H$_{35}$O$_8$F: Calculated (%): C, 64.02; H, 6.96; F, 3.75. Found (%): C, 63.93; H, 6.95; F, 3.73.

EXAMPLE 2

50.7 g (0.1 mole) of compound ⑧′ was dissolved in 500 ml of tetrahydrofuran, and 100 ml of a 20% aqueous solution of potassium carbonate was added. While the solution was stirred at room temperature, sodium borohydride was added to the solution. When the disappearance of compound ⑧′ was determined by thin-layer chromatography, the reaction mixture was separated by adding water and chloroform. The organic layer was washed with water, and concentrated under reduced pressure. The crude crystals were recrystallized from methanol to give 45.9 g (90%) of compound ⑨′ as white crystals.

Melting point: 125.8°-126.3° C. (decomp.).

IR, cm$^{-1}$(KBr): 3510(m)($\nu$OH); 1760(s), 1735(s)($\nu$C=O); 1650(w)($\nu$C=C); 1237(s)($\nu$C—O—C).

H$^1$NMR, $\delta$(CDCl$_3$): 0.94(3H, s, 18CH$_3$), 1.37(3H, s, 19CH$_3$), 2.06(3H, s, CH$_3$CO—), 2.15(3H, s, CH$_3$CO—), 3.91(4H, s, —OCH$_3$CH$_2$O—), 4.25-4.55(1H, m, C-11H), 4.61(1H, d, J=17 Hz, —COCH$_2$OAC), 4.89(1H, d, J=17 Hz, —COCH$_2$OAC), 5.16-5.40(1H, m, C-6H).

Elemental analysis for C$_{27}$H$_{37}$O$_8$F: Calculated (%): C, 63.76; H, 7.33; F, 3.74. Found (%): C, 63.99; H. 7.37; F, 3.71.

EXAMPLE 3

37.8 g (0.18 mole) of trifluoroacetic anhydride was added to a suspension composed of 4.1 ml (0.15 mole) of 90% hydrogen peroxide and 100 ml of methylene chloride under ice cooling. Ten minutes later, the mixture was cooled to −10° to −20° C. With stirring, 50.9 g (0.1 mole) of compound ⑨′ was slowly added. After the reaction was performed at this temperature for 10 hours, the reaction mixture was poured into a 5% aqueous solution of sodium bicarbonate. Methylene chloride was added to separate the mixture. The organic layer was concentrated under reduced pressure, and recrystallized from benzene-hexane to give 41.9 g (yield 80%) of compound ⑩ ' as white crystals.

Melting point: 193° C. (decomp.).

IR, cm$^{-1}$(KBr): 3455(m)($\nu$OH); 1755(s), 1740(s)($\nu$C=O); 1235(s), 1230(s)($\nu$C—O—C).

H$^1$NMR, $\delta$(d$_6$—DMSO): 0.77(3H, s, 18CH$_3$), 1.36(3H, s, 19CH$_3$), 2.03(3H, s, CH$_3$CO—), 2.08(3H, s, CH$_3$CO—), 3.75-3.82(4H, m, —OCH$_2$CH$_2$O—), 3.8-4.2(1H, m, C-11H), 4.73(2H, s, —COCH$_2$OAc), 5.03(1H, d, J=4.5 Hz, C-11OH).

Elemental analysis for C$_{27}$H$_{37}$O$_9$F: Calculated (%): C, 61.82; H, 7.11; F, 3.62. Found (%): C, 61.78; H, 7.13; F, 3.59.

EXAMPLE 4

In the same way as in Example 3, 40.8 g (yield 78%) of compound ⑭ ' as white crystals was obtained from 50.7 g (0.1 mole) of compound ⑧.

Melting point: 173.8°-177.8° C.

IR, cm$^{-1}$(KBr): 1760(s), 1750(s), 1730(s)($\nu$C=O); 1240(s)($\nu$C—O—C).

H$^1$NMR, $\delta$(CDCl$_3$): 0.64(3H, s, 18CH$_3$), 1.29(3H, s, 19CH$_3$), 2.13(6H, s, CH$_3$CO—), 2.85(1H, s, C-6H), 3.70-4.10(4H, m, —OCH$_2$CH$_2$O—), 4.61(1H, d, J=16.5 Hz, —(OCH$_2$OAc), 4.76(1H, d, J=16.5 Hz, —COCH$_2$OAc).

Elemental analysis for C$_{27}$H$_{35}$O$_9$F: Calculated (%): C, 62.06; H, 6.75; F, 3.64. Found (%): C, 61.88; H, 6.76; F, 3.62.

EXAMPLE 5

In the same way as in Example 2, 47.2 g (yield 90%) of compound ⑩ ' as white crystals was obtained from 52.3 g (0.1 mole) of compound ⑭ '. The product had the same properties as the product obtained in Example 3.

EXAMPLE 6

250 ml of a 65% aqueous solution of hydrogen fluoride was cooled to −70° to −80° C. With stirring, 52.5 g of compound ⑩ ' was added slowly over the course of about 3 hours. The mixture was stirred at the same temperature for one hour, and poured into 2.5 liters of cold water. The precipitated crystals were separated by filtration, and washed with water until the washing became neutral. The resulting crystals were dried and recrystallized from methylene chloride to give 35.0 g (yield 70%) of compound ⑪ ' as white crystals.

Melting point: 119.5°-120.0° C. (decomp.).

IR, cm$^{-1}$(KBr): 3600(m), 3500(m)($\nu$OH); 1735(s)($\nu$OH); 1240(s)($\nu$C—O—C).

H$^1$NMR, $\delta$(CDCl$_3$): 0.99(3H, s, 18CH$_3$), 1.61(3H, d, J=4.5 Hz, 19CH$_3$), 2.08(3H, s, CH$_3$CO—), 2.14(3H, s, CH$_3$CO—), 4.34(1H, dm, J=49 Hz, C-6H), 4.20-4.55(1H, m, C-11H), 4.64(1H, d, J=17 Hz, —COCH$_2$OAC), 4.90(1H, d, J=17 Hz, —COCH$_2$OAC).

Elemental analysis for C$_{25}$H$_{34}$O$_8$F$_2$: Calculated (%): C, 59.99; H, 6.85; F, 7.59. Found (%): C, 60.13; H, 6.79; F, 7.52.

EXAMPLE 7

In the same way as in Example 6, 34.9 g (yield 70%) of compound ⑮ ' as white crystals was obtained from 52.3 g (0.1 mole) of compound ⑭ '.

Melting point: 217.5°-217.8° C. (decomp.).

IR, cm$^{-1}$(KBr): 3625(m)($\nu$OH); 1755(s), 1740(s), 1725(s)($\nu$C=O); 1233(s)($\nu$C—O—C).

H$^1$NMR, $\delta$(CDCl$_3$): 0.76(3H, s, 18CH$_3$), 1.50(3H, d, J=3 Hz, 18CH$_3$), 2.13(3H, s, CH$_3$CO—), 2.16(3H, s, CH$_3$CO—), 4.37(1H, dm, J=48 Hz, C-6H), 4.68(1H, d, J=16.5 Hz, —COCH$_2$OAC), 4.79(1H, d, J=16.5 Hz, —COCH$_2$OAC).

Elemental analysis for C$_{25}$H$_{32}$O$_8$F$_2$: Calculated (%): C, 60.23; H, 6.47; F, 7.62. Found (%): C, 60.40; H, 6.43; F, 7.56.

EXAMPLE 8

50.1 g (0.1 mole) of compound ⑪ ' and 50 g of sodium acetate were added to 250 ml of acetic acid, and the mixture was heated to 90° C. After sodium acetate dissolved, a solution of 16.8 g (0.105 mole) of bromine in 50 ml of acetic acid was added dropwise over the course of about 5 minutes. When the color of the added bromine disappeared, a solution of 16.8 g (0.105 mole) of bromine in 50 ml of acetic acid was added to a time. When the color of the added bromine disappeared, the reaction mixture was immediately cooled to room temperature and poured into 3.5 liters of cold water. The precipitated crystals were separated by filtration, and dried to give 62.5 g (yield 95%) of compound ⑫ ' as pale yellow crystals.

Melting point: 136.2°-137.0° C. (decomp.).

IR, cm$^{-1}$(KBr): 3590(m), 3450(m)($\nu$OH); 1755(s), 1740(s), 1720(s)($\nu$C=O); 1245(s)($\nu$C—O—C).

H$^1$NMR, $\delta$(CDCl$_3$): 1.00(3H, s, 18CH$_3$), 1.85(3H, d, J=5.5 Hz, 19CH$_3$), 2.08(3H, s, CH$_3$CO—), 2.17(3H, s, CH$_3$CO—), 4.40-4.45(1H, m, C-11H), 4.41(1H, dm, J=49 Hz, C-6H, 4.63(1H, d, J=17 Hz, —COCH$_2$OAC), 4.91(1H, d, J=17 Hz, —COCH$_2$OAC).

Elemental analysis for C$_{25}$H$_{32}$O$_8$Br$_2$F$_2$: Calculated (%): C, 45.61; H, 4.90; Br, 24.27; F, 5.77. Found (%): C, 45.39; H, 4.97; Br, 24.21; F, 5.70.

EXAMPLE 9

In the same way as in Example 8, 62.3 g (yield 95%) of compound ⑯ ' as pale yellow crystals was obtained form 49.9 g (0.1 mole) of compound ⑮ '.

Melting point: 132.6°-133.7° C. (decomp.).

IR, cm$^{-1}$(KBr): 3600(m)($\nu$OH); 1755(s), 1740(s), 1730(s)($\nu$C=O); 1240($\nu$C—O—C).

H$^1$NMR, $\delta$(CDCl$_3$): 0.76(3H, s, 18CH$_3$), 1.75(3H, d, J=3 Hz, 19CH$_3$), 2.13(3H, s, CH$_3$CO—), 2.16(3H, s, CH$_3$CO—), 4.45(1H, dm, J=45.5 Hz, C-6H), 4.69(1H, d, J=18 Hz, —COCH$_2$OAC), 4.81(1H, d, J=8 Hz, —COCH$_2$OAC).

Elemental analysis for C$_{25}$H$_{30}$O$_8$Br$_2$F$_2$: Calculated (%): C, 45.75; H, 4.61; Br, 24.35; F, 5.79 Found (%): C, 45.91; H, 4.60; Br, 24.17; F, 5.74

EXAMPLE 10

Anhydrous lithium chloride (65 g) was added to 650 ml of N,N-dimethylformamide, and the mixture was heated to 110° to 120° C. to form a solution. To the solution was added 65.8 g of compound ⑫ ' at the same temperature. The mixture was stirred for 2 hours. The reaction mixture was cooled to room temperature, and poured into 6.5 liters of water. The resulting precipitate was separated by filtration, and washed with water. The resulting crude crystals were dried, and separated by silica gel column chromatography. 38.6 g (yield 69%) of compound ⑬ ' as white crystals was obtained from fractions obtained by elution with chloroform-ethyl acetate (10:1).

Melting point: 298° C. (decomp.).

Mass: M+=558.

IR, cm⁻¹(KBr): 3520(m)($\nu$OH); 1758(s), 1733(s), 1705(s), 1650(s)($\nu$C=O); 1235(s)($\nu$C—O—C).

H¹NMR, $\delta$(d$_6$-DMSO): 0.91(3H, s, 18CH$_3$), 1.60(3H, d, J=3.4 Hz, 19CH$_3$), 2.01(3H, s, CH$_3$CO—), 2.12(3H, s, CH$_3$CO—), 4.1–4.4(1H, broad, C-11H), 4.80(2H, s, —COCH$_2$OAC), 5.39 (1H, dm, J=51 Hz, C-6H), 5.63(1H, d, J=6 Hz, C-11OH), 6.51 (1H, d, J=4 Hz, C-4H), 7.85(1H, s, C-1H).

Elemental analysis for C$_{25}$H$_{29}$O$_7$BrF$_2$: Calculated (%): C, 53.68; H, 5.23; Br, 14.28; F, 6.79 Found (%): C, 53.46; H, 5.23; Br, 14.21; F, 6.74

EXAMPLE 11

In the same way as in Example 10, 39.5 g (yield 71%) of compound ⑰' as white crystals was obtained from 65.6 g (0.1 mole) of compound ⑯'.

Melting point: 262.7°–263.5° C. (decomp.).

IR, cm⁻¹(KBr): 1750(s), 1740(s), 1676(s)($\nu$C=O); 1640(m), 1601(m)($\nu$C=C); 1233(s)($\nu$C—O—C).

H¹NMR, $\delta$(CDCl$_3$): 0.78(3H, s, 18CH$_3$), 1.63(3H, d, J=2 Hz, 19CH$_3$), 2.07(3H, s, CH$_3$CO—), 2.12(3H, s, CH$_3$CO—), 4.67(1H, d, J=17.5 Hz, —COCH$_2$OAC), 4.80(1H, d, J=17.5 Hz, —COCH$_2$OAC), 5.20(1H, dm, J=49 Hz, C-6H), 6.38(1H, d, J=7 Hz, C-4H), 7.88(1H, s, C-1H).

Elemental analysis for C$_{25}$H$_{27}$O$_9$BrF$_2$: Calculated (%): C, 53.87; H, 4.88; Br, 14.34; F, 6.82 Found (%): C, 54.03; H, 4.79; Br, 14.15; F, 6.77

EXAMPLE 12

In the same way as in Example 2, 44.7 g (yield 80%) of compound ⑬' as white crystals was obtained from 55.7 g (0.1 mole) of compound ⑰'. The product showed the same properties as the product obtained in Example 10.

What is claimed is:

1. A process for preparing a 2-bromo-6$\beta$,9$\alpha$-difluoro-11$\beta$,17$\alpha$,21-trihydroxy-1,4-pregnadien-3,20-dione-17,21-diester (compound ⑬) represented by the general formula

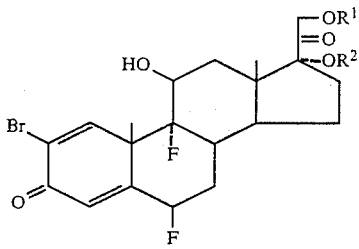

wherein OR¹ and OR² are identical or different, and each represents an acyloxy group or a sulfuric or phosphoric acid ester residue, which comprises (A) reacting a 17$\alpha$,21-dihydroxy-9$\alpha$-fluoro-4-pregnen-3,11,20-trione-17,21-diester (compound ⑦) represented by the general formula

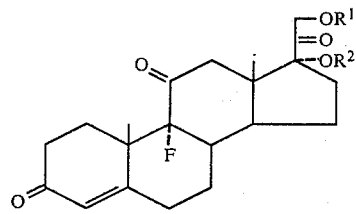

wherein OR¹ and OR² are as defined above, with a ketalizing agent to prepare a 17$\alpha$,20,21-dihydroxy-3,3-ethylenedioxy-9$\alpha$-fluoro-5-pregnen-11,20-dione-17,21-diester (compound ⑧), and (B) thereafter preparing the compound ⑬ by
  (i) reducing the compound ⑧ to form a 11$\beta$-hydroxy compound (compound ⑨), reacting the hydroxy compound with a peracid to form a 5$\alpha$,6$\alpha$-epoxy compound (compound ⑩), reacting the epoxy compound with hydrogen fluoride to form a 6$\beta$-fluoro-5$\alpha$-hydroxy-3-keto compound (compound ⑪), brominating the keto compound to form a 2,2-dibromo compound (compound ⑫), and dehydrobrominating and then dehydrating the dibromo compound to form the compound ⑬, or
  (ii) treating the compound ⑧ with a peracid to form a 5$\alpha$,6$\alpha$-epoxy compound (compound ⑭), reducing the epoxy compound to form a 11$\beta$-hydroxy compound (compound ⑩), reacting the hydroxy compound with hydrogen fluoride to form a 6$\beta$-fluoro-5$\alpha$-hydroxy-3-keto compound (compound ⑪), brominating the keto compound to form a 2,2-dibromo compound (compound ⑫), and dehydrobrominating and then dehydrating the dibromo compound to form the compound ⑬, or
  (iii) treating the compound ⑧ with a peracid to form a 5$\alpha$,6$\alpha$-epoxy compound (compound ⑭), reacting the epoxy compound with hydrogen fluoride to form a 6$\beta$-fluoro-5$\alpha$-hydroxy-3-keto compound (compound ⑮), brominating the keto compound to form a 2,2-dibromo compound (compound ⑯), dehydrobrominating and then dehydrating the dibromo compound to form a 1,4-diene compound (compound ⑰), and reducing the diene compound to form the compound ⑬.

2. The process of claim 1 wherein the 17$\alpha$,21-dihydroxy-9$\alpha$-fluoro-4-pregnen-3,11,20-trione-17,21-diester (compound ⑦) used as a starting material is prepared by reacting a 17$\alpha$,21-dihydroxy-4,9(11)-pregnadien-3,20-dione-17,21-diester with hypochlorous acid or hydrobromous acid to form a halohydrin compound (compound ④), reacting the halohydrin with a basic substance to form a 9$\beta$,11$\beta$-epoxy compound (compound ⑤), reacting the epoxy compound with hydrogen fluoride to form a 9$\alpha$-fluoro-11$\beta$-hydroxy compound (compound ⑥), and oxidizing the hydroxy compound to convert it to a 11-keto compound.

3. A steroid represented by the following general formula

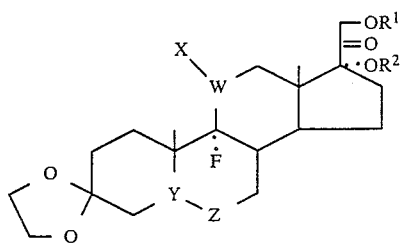
(I)

wherein >W—X represents >C=O or >CH—OH, >Y—Z represents

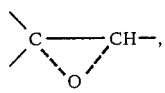

$OR^1$ and $OR^2$ are identical or different and each represents an acyloxy group or a sulfonic or phosphoric acid residue.

4. A steroid represented by the general formula

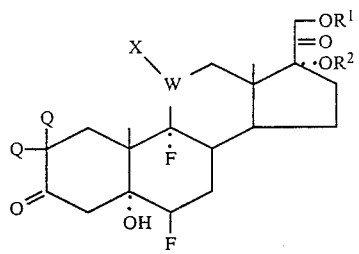
(II)

wherein Q represents a hydrogen or bromine atom, >W—X represents >C=O or >CH—OH, $OR^1$ and $OR^2$ are identical of different and each represents an acyloxy group or a sulfuric or phosphoric acid residue.

5. The process of claim 1 wherein the ketalizing agent in step (A) is ethylene glycol, acetone ethylene ketal, mesityl oxide, ethylene ketal, or ethylene glycol di-trimethylsilyl ether, said ketalizing reaction to prepare the compound 8 being carried out in an organic solvent in the presence of an acid catalyst at a temperature in the range of from −20° C. to 100° C.

6. The method of claim 1 which comprises the steps (A) and (B)(i).

7. The method of claim 1 which comprises the steps (A) and (B)(ii).

8. The method of claim 1 which comprises the steps (A) and (B)(iii).

9. The steroid of claim 3 having the formula:

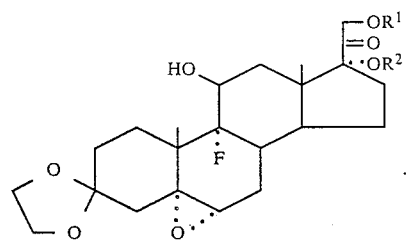

10. The steroid of claim 3 having the formula:

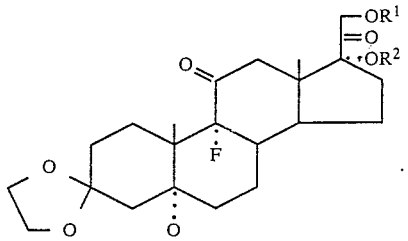

11. The steroid according to claim 4 which is represented by the formula:

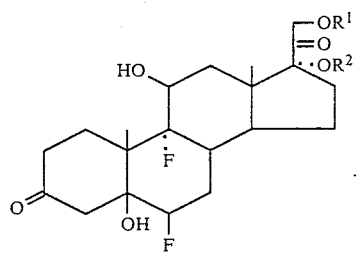

12. The steroid according to claim 4 which is represented by the formula:

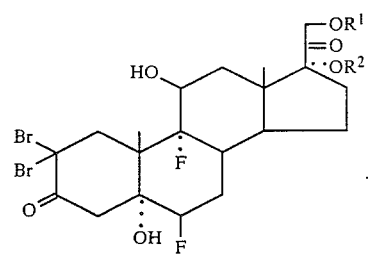

13. The steroid according to claim 4 which is represented by the formula:

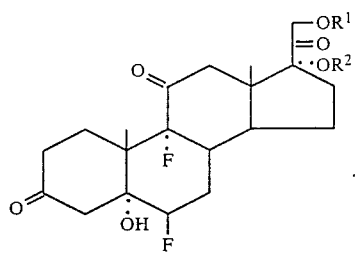

14. The steroid according to claim 4 which is represented by the formula:

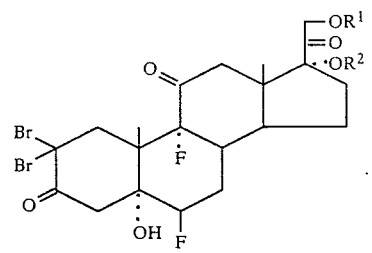

* * * * *

UNITED STATES PATENT AND TRADEMARK OFFICE
CERTIFICATE OF CORRECTION

PATENT NO. : 4,525,303
DATED : June 25, 1985
INVENTOR(S) : TAKAGAKI ET AL.

It is certified that error appears in the above-identified patent and that said Letters Patent is hereby corrected as shown below:

Claim 1, line 14, delete "20".

Claim 2, line 5, delete "hydrobromous", insert --hypobromous--.

Claim 10, line 2, delete the formula, and insert therefor;

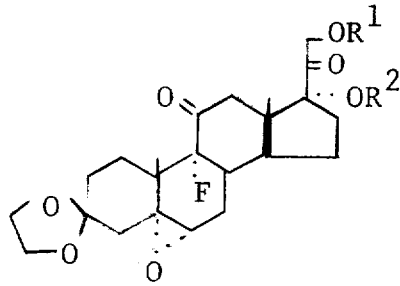

Claim 11, line 3, delete the formula, and insert therefor:

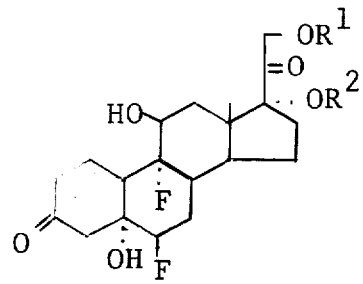

Signed and Sealed this

Fifteenth Day of October 1985

[SEAL]

Attest:

DONALD J. QUIGG

Attesting Officer

Commissioner of Patents and Trademarks—Designate